(12) United States Patent
Butcher

(10) Patent No.: US 7,946,236 B2
(45) Date of Patent: May 24, 2011

(54) USING ZIGZAGS TO CREATE THREE-DIMENSIONAL EMBROIDERED STRUCTURES

(75) Inventor: Peter Butcher, Nottingham (GB)

(73) Assignee: NuVasive, Inc., San Diego, CA (US)

( * ) Notice: Subject to any disclaimer, the term of this patent is extended or adjusted under 35 U.S.C. 154(b) by 474 days.

(21) Appl. No.: 11/968,157

(22) Filed: Dec. 31, 2007

(65) Prior Publication Data

US 2008/0178786 A1 Jul. 31, 2008

Related U.S. Application Data

(60) Provisional application No. 60/898,892, filed on Jan. 31, 2007.

(51) Int. Cl.
*B32B 7/08* (2006.01)
*A61B 17/70* (2006.01)
*D05B 93/00* (2006.01)

(52) U.S. Cl. .................. 112/475.18; 112/439; 112/403; 112/157; 606/246

(58) Field of Classification Search ............. 112/475.18, 112/475.22, 403, 415, 416, 439, 440, 157; 428/906.6; 2/243.1; 606/151–157, 246–249
See application file for complete search history.

(56) References Cited

U.S. PATENT DOCUMENTS

| 889,614 | A | * | 6/1908 | Johnsen | 112/475.18 |
|---|---|---|---|---|---|
| 924,795 | A | * | 6/1909 | Klemm et al. | 112/475.22 |
| 3,859,941 | A | | 1/1975 | Krieger | |
| 3,867,728 | A | | 2/1975 | Stubstad et al. | |
| 3,875,595 | A | | 4/1975 | Froning | |
| 4,280,954 | A | | 7/1981 | Yannas et al. | |
| 4,309,777 | A | | 1/1982 | Patil | |
| 4,349,921 | A | | 9/1982 | Kuntz | |
| 4,415,617 | A | | 11/1983 | D'Elia | |
| 4,458,678 | A | | 7/1984 | Yannas et al. | |
| 4,512,038 | A | | 4/1985 | Alexander et al. | |
| 4,517,910 | A | * | 5/1985 | Jalowsky | 112/439 |
| 4,714,469 | A | | 12/1987 | Kenna | |
| 4,728,329 | A | | 3/1988 | Mansat | |
| 4,759,766 | A | | 7/1988 | Buettner-Janz | |
| 4,759,769 | A | | 7/1988 | Hedman et al. | |
| 4,772,287 | A | | 9/1988 | Ray et al. | |
| 4,776,851 | A | | 10/1988 | Bruchman et al. | |
| 4,790,850 | A | | 12/1988 | Dunn et al. | |

(Continued)

FOREIGN PATENT DOCUMENTS

DE 703123 C 1/1941

(Continued)

OTHER PUBLICATIONS

Notification of Transmittal of the International Search Report and the Written Opinion of the International Searching Authority in the corresponding International Application PCT/US2008/052524 mailed Jan. 30, 2008.

*Primary Examiner* — Ismael Izaguirre
(74) *Attorney, Agent, or Firm* — Jonathan Spangler; Marjorie Jarvis

(57) ABSTRACT

An embroidery process allowing for extra lengths of stitched thread pairs to be laid down in a zigzag pattern while embroidering on a dissolvable substrate such that when the substrate is removed, the extra length allows the two-dimensional embroidered structure to relax into a three-dimensional shape.

10 Claims, 6 Drawing Sheets

U.S. PATENT DOCUMENTS

| | | | |
|---|---|---|---|
| 4,863,476 A | 9/1989 | Shepperd | |
| 4,863,477 A | 9/1989 | Monson | |
| 4,880,429 A | 11/1989 | Stone | |
| 4,904,260 A | 2/1990 | Ray et al. | |
| 4,905,692 A | 3/1990 | More | |
| 4,911,718 A | 3/1990 | Lee et al. | |
| 4,917,704 A | 4/1990 | Frey et al. | |
| 4,932,969 A | 6/1990 | Frey et al. | |
| 4,932,975 A | 6/1990 | Main et al. | |
| 4,946,377 A | 8/1990 | Kovach | |
| 4,946,378 A | 8/1990 | Hirayama et al. | |
| 4,955,908 A | 9/1990 | Frey et al. | |
| 5,002,576 A | 3/1991 | Fuhrmann et al. | |
| 5,004,474 A | 4/1991 | Fronk et al. | |
| 5,007,926 A | 4/1991 | Derbyshire | |
| 5,007,934 A | 4/1991 | Stone | |
| 5,047,055 A | 9/1991 | Bao et al. | |
| 5,108,438 A | 4/1992 | Stone | |
| 5,108,937 A | 4/1992 | White | |
| 5,123,926 A | 6/1992 | Pisharodi | |
| 5,171,280 A | 12/1992 | Baumgartner | |
| 5,171,281 A | 12/1992 | Parsons et al. | |
| 5,192,322 A | 3/1993 | Koch et al. | |
| 5,192,326 A | 3/1993 | Bao et al. | |
| 5,246,458 A | 9/1993 | Graham | |
| 5,258,043 A | 11/1993 | Stone | |
| 5,306,308 A | 4/1994 | Gross et al. | |
| 5,306,309 A | 4/1994 | Wagner et al. | |
| 5,383,884 A | 1/1995 | Summers | |
| 5,401,269 A | 3/1995 | Buttner-Janz et al. | |
| 5,443,499 A | 8/1995 | Schmitt | |
| 5,458,636 A | 10/1995 | Brancato | |
| 5,458,643 A | 10/1995 | Oka et al. | |
| 5,507,816 A | 4/1996 | Bullivant | |
| 5,522,898 A | 6/1996 | Bao | |
| 5,534,028 A | 7/1996 | Bao et al. | |
| 5,534,030 A | 7/1996 | Navarro et al. | |
| 5,540,688 A | 7/1996 | Navas | |
| 5,540,703 A | 7/1996 | Barker, Jr. et al. | |
| 5,545,229 A | 8/1996 | Parsons et al. | |
| 5,549,679 A | 8/1996 | Kuslich | |
| 5,562,736 A | 10/1996 | Ray et al. | |
| 5,562,738 A | 10/1996 | Boyd et al. | |
| 5,571,189 A | 11/1996 | Kuslich | |
| 5,609,119 A * | 3/1997 | Yeh | 112/475.23 |
| 5,645,597 A | 7/1997 | Krapiva | |
| 5,674,296 A | 10/1997 | Bryan et al. | |
| 5,676,702 A | 10/1997 | Ratron | |
| 5,683,464 A | 11/1997 | Wagner et al. | |
| 5,683,465 A | 11/1997 | Shinn et al. | |
| 5,702,450 A | 12/1997 | Bisserie | |
| 5,702,454 A | 12/1997 | Baumgartner | |
| 5,705,780 A | 1/1998 | Bao | |
| 5,716,416 A | 2/1998 | Lin | |
| 5,755,796 A | 5/1998 | Ibo et al. | |
| 5,794,555 A * | 8/1998 | Kwang | 112/475.22 |
| 5,800,543 A | 9/1998 | McLeod et al. | |
| 6,093,205 A | 7/2000 | McLeod et al. | |
| 6,110,210 A | 8/2000 | Norton et al. | |
| 6,174,330 B1 | 1/2001 | Stinson | |
| 6,248,106 B1 | 6/2001 | Ferree | |
| 6,263,817 B1 * | 7/2001 | Tajima et al. | 112/475.22 |
| 6,283,998 B1 | 9/2001 | Eaton | |
| 6,368,326 B1 | 4/2002 | Dakin et al. | |
| 6,371,990 B1 | 4/2002 | Ferree | |
| 6,416,776 B1 | 7/2002 | Shamie | |
| 6,419,704 B1 | 7/2002 | Ferree | |
| 6,428,544 B1 | 8/2002 | Ralph et al. | |
| 6,447,548 B1 | 9/2002 | Ralph et al. | |
| 6,592,625 B2 | 7/2003 | Cauthen | |
| 6,620,196 B1 | 9/2003 | Trieu | |
| 6,712,853 B2 | 3/2004 | Kuslich | |
| 6,746,485 B1 | 6/2004 | Zucherman et al. | |
| 6,893,466 B2 | 5/2005 | Trieu | |
| 6,925,947 B2 * | 8/2005 | Lin et al. | 112/475.22 |
| 6,955,689 B2 | 10/2005 | Ryan et al. | |
| 7,004,970 B2 | 2/2006 | Cauthen II et al. | |
| 7,214,225 B2 * | 5/2007 | Ellis et al. | 606/60 |
| 7,338,531 B2 * | 3/2008 | Ellis et al. | 623/23.74 |
| 7,341,601 B2 | 3/2008 | Eisermann et al. | |
| 7,445,634 B2 | 11/2008 | Trieu | |
| 7,588,574 B2 | 9/2009 | Assell et al. | |
| 7,713,463 B1 * | 5/2010 | Reah et al. | 264/490 |
| 2001/0027319 A1 | 10/2001 | Ferree | |
| 2002/0077702 A1 | 6/2002 | Castro | |
| 2003/0074075 A1 | 4/2003 | Thomas, Jr. et al. | |
| 2003/0078579 A1 | 4/2003 | Ferree | |
| 2003/0129257 A1 | 7/2003 | Nies et al. | |
| 2003/0220691 A1 | 11/2003 | Songer et al. | |
| 2004/0039392 A1 | 2/2004 | Trieu | |
| 2004/0078089 A1 | 4/2004 | Ellis et al. | |
| 2004/0113801 A1 | 6/2004 | Gustafson et al. | |
| 2004/0243237 A1 | 12/2004 | Unwin et al. | |
| 2005/0027364 A1 | 2/2005 | Kim et al. | |
| 2005/0119725 A1 | 6/2005 | Wang et al. | |
| 2005/0177240 A1 | 8/2005 | Blain | |
| 2005/0192669 A1 | 9/2005 | Zdeblick et al. | |
| 2005/0228500 A1 | 10/2005 | Kim et al. | |
| 2006/0085080 A1 | 4/2006 | Bechgaard et al. | |
| 2006/0116774 A1 | 6/2006 | Jones et al. | |
| 2006/0179652 A1 | 8/2006 | Petersen et al. | |
| 2006/0200137 A1 | 9/2006 | Soboleski et al. | |
| 2006/0293662 A1 | 12/2006 | Boyer, II et al. | |
| 2007/0055373 A1 | 3/2007 | Hudgins et al. | |
| 2007/0100453 A1 | 5/2007 | Parsons et al. | |
| 2007/0112428 A1 | 5/2007 | Lancial | |
| 2007/0204783 A1 * | 9/2007 | Chong | 112/475.22 |

FOREIGN PATENT DOCUMENTS

| | | |
|---|---|---|
| DE | 383005 C1 | 11/1989 |
| DE | 4315757 C1 | 11/1994 |
| EP | 0117072 A1 | 1/1984 |
| EP | 0192949 A1 | 9/1986 |
| EP | 0260970 A2 | 3/1988 |
| EP | 0179695 B1 | 3/1989 |
| EP | 0314412 A1 | 5/1989 |
| EP | 0328401 A1 | 8/1989 |
| EP | 0334045 A1 | 9/1989 |
| EP | 0346129 A1 | 12/1989 |
| EP | 0346269 A2 | 12/1989 |
| EP | 0453393 A1 | 10/1991 |
| EP | 0298235 B1 | 12/1991 |
| EP | 0459914 A1 | 12/1991 |
| EP | 0621017 A1 | 4/1994 |
| EP | 0599419 A2 | 6/1994 |
| EP | 0621010 A1 | 10/1994 |
| EP | 0662309 A1 | 7/1995 |
| EP | 0563332 B1 | 8/1995 |
| EP | 0820740 A1 | 1/1996 |
| EP | 0744162 A2 | 11/1996 |
| EP | 0747025 A1 | 12/1996 |
| EP | 1318167 A2 | 6/2003 |
| FR | 2638349 A1 | 5/1988 |
| FR | 2688691 A1 | 9/1993 |
| FR | 2690073 A1 | 10/1993 |
| FR | 2696338 A1 | 4/1994 |
| FR | 2700810 A3 | 7/1994 |
| FR | 2710520 A1 | 4/1995 |
| FR | 2710829 A1 | 4/1995 |
| GB | 2270264 A | 3/1994 |
| GB | 2276823 A | 10/1994 |
| WO | WO 90/11735 A1 | 10/1990 |
| WO | WO 90/12551 A1 | 11/1990 |
| WO | WO 91/00713 A1 | 1/1991 |
| WO | WO 91/03993 A1 | 4/1991 |
| WO | WO 92/03988 A1 | 3/1992 |
| WO | WO 92/10218 A1 | 6/1992 |
| WO | WO 92/10982 A1 | 7/1992 |
| WO | WO 93/16664 A1 | 9/1993 |
| WO | WO 93/17635 A1 | 9/1993 |
| WO | WO 95/19153 A1 | 7/1995 |
| WO | WO 95/25487 A1 | 9/1995 |
| WO | WO 95/31946 A1 | 11/1995 |
| WO | WO 96/11639 A1 | 4/1996 |
| WO | WO 96/11642 A1 | 4/1996 |
| WO | WO 96/40014 A1 | 12/1996 |
| WO | WO 97/20526 A1 | 6/1997 |

| | | | | | | | |
|---|---|---|---|---|---|---|---|
| WO | WO 99/37242 | A1 | 7/1999 | WO | WO 2005/092211 | A1 | 10/2005 |
| WO | WO 01/21246 | A1 | 3/2001 | WO | WO 2005/092247 | A1 | 10/2005 |
| WO | WO 01/30269 | A1 | 5/2001 | WO | WO 2005/092248 | A1 | 10/2005 |
| WO | WO 02/11650 | A1 | 2/2002 | WO | WO 2005/133130 | A2 | 12/2006 |
| WO | WO 02/30306 | A1 | 4/2002 | WO | WO 2007/012070 | A2 | 1/2007 |
| WO | WO 02/30324 | A1 | 4/2002 | WO | WO 2007/020449 | A2 | 2/2007 |
| WO | WO 03/06811 | A1 | 8/2003 | WO | WO 2007/067547 | A2 | 6/2007 |
| WO | WO 2004/002374 | A1 | 1/2004 | | | | |
| WO | WO 2005/004941 | A1 | 1/2005 | | | | |

* cited by examiner

USING ZIGZAGS TO CREATE THREE-DIMENSIONAL EMBROIDERED STRUCTURES

CROSS REFERENCES TO RELATED APPLICATIONS

The present application is a nonprovisional patent application claiming benefit under 35 U.S.C. §119(e) from U.S. Provisional Application Ser. No. 60/898,892, filed on Jan. 31, 2007, the entire contents of which are hereby expressly incorporated by reference into this disclosure as if set forth fully herein.

BACKGROUND OF THE INVENTION

I. Field of the Invention

The present invention relates to medical devices and methods generally aimed at surgical implants. In particular, the disclosed system and associated methods are related to a manner of creating surgical implants via embroidery.

II. Discussion of the Prior Art

Embroidered structures are created on substrates. Some substrates are designed to stay in place with the embroidered structure while other substrates are removed at the end of the embroidery process. All of the embroidered structures discussed below are created on removable substrates, specifically ones removed through processes of dissolution.

On a dissolvable substrate, a plurality of parallel, stationary backing threads are placed and secured on one surface of a dissolvable substrate, called the backing surface. On the opposing surface of the substrate, called the stitching surface, is a plurality of stitching threads with one-to-one correspondence to the backing threads. Stitching may be done between one pair of threads at a time or in simultaneous multiplicity, as is described below.

The plurality of stitching threads from the stitching surface are passed through openings created in the dissolvable substrate by the passing of each individual thread to the backing surface. Each stitching thread is then looped over its corresponding backing thread, in essence picking up the backing thread, forming a lock stitch. Once each stitching thread has picked up its corresponding backing thread, the plurality of stitching threads are passed from the backing surface to the stitching surface through the openings in the dissolvable substrate created during the passage to the backing surface. The lock stitches prevent the stitching threads from completely pulling back out of the openings created in the dissolvable substrate. The plurality of stitching threads is then moved to a new stitching site and the process repeats until all the backing threads are joined by lock stitches to the corresponding stitching threads, creating a plurality of thread pairs.

A plurality of thread pairs may be enclosed by one or more pluralities of enclosing thread pairs. To enclose a plurality of thread pairs, a plurality of enclosing backing threads is placed and secured on the backing surface of a dissolvable substrate already holding at least one plurality of thread pairs, such that the plurality of enclosing backing threads covers the previously stitched plurality of backing threads. A plurality of enclosing backing threads is usually not parallel with the previous plurality of backing and stitching threads. A plurality of enclosing stitching threads, with one-to-one correspondence to the plurality of enclosing backing threads, is then stitched to the plurality of enclosing backing threads by the stitching process described above.

When the enclosing backing threads are all joined to the enclosing stitching threads by lock stitches, a plurality of enclosing thread pairs has been formed. This process may be repeated by stitching even more pluralities of enclosing thread pairs over all the previously stitched thread pairs, such that the first plurality is enclosed by the second plurality, which is enclosed by a third plurality, which is enclosed by a fourth plurality, etc. This process produces stable embroidered structures which do not unstitch into a pile of threads when the dissolvable substrate is removed.

The process of dissolvable substrate removal is dependent upon the material from which the dissolvable substrate is composed. Substrate materials are chosen such that the dissolution process which removes the dissolvable substrate will minimally affect the physical properties of the remaining embroidered structure. The embroidered structure remains intact despite the removal of the dissolvable substrate because each stitching thread is stitched to its corresponding backing thread, and vice versa, which is enclosed in one or more pluralities of enclosing thread pairs, all of which provides structural support. The result of the stitching is the creation of a generally two dimensional embroidered structure. There are, however, applications where it would be advantageous to have a generally three-dimensional embroidered structure rather than a generally two-dimensional embroidered structure, but the processes by which three-dimensional embroidered structures may be formed have been complicated and not conducive to cost effective and repeatable mass production.

The first type of process for creating three-dimensional embroidered structures has been to build up the structural shape of the embroidered structure with layer upon layer of embroidered thread. The drawbacks to this technique are: it makes the embroidered structure thicker where the building up has been done; the building up only yields block-type structures and does not allow for the embroidering of curvatures; and this layering process must be done three-dimensionally, which excludes the use of a cost effective, repeatable form of mass production such as an automated embroidery machine.

A second process of manufacturing three-dimensional embroidered structures takes two or more generally flat embroidered structures and stitches them together such that they form a three-dimensional structure. While preserving the uniform thickness of the embroidered structures lost by the layering technique above and allowing for the simplicity of embroidering each flat section in two-dimensions, this process requires several stitching steps which must be done three-dimensionally after the embroidering of the sections is completed. This process is costly with repeatability concerns where the final results and dimensions will be subject to the skill and dexterity of the individual who performs the stitching.

A third known process creates a single, generally two-dimensional embroidered structure which may be folded such that the edge or edges of the structure meet and may be stitched together to form a three-dimensional structure. However, this process suffers from the same post-embroidering stitching steps in three-dimensions as the second process, and thus suffers from the same drawbacks.

The present invention is intended to deal with these and other limitations of creating three-dimensional embroidered structures cost effectively and repeatably.

SUMMARY OF THE INVENTION

According to the present invention, there is an embroidery process by which a three-dimensional embroidered structure may be embroidered on a two-dimensional, dissolvable substrate and as such may be mass produced in a cost effective and reproducible manner.

According to one embodiment, the present invention may include three-dimensional embroidered structures which may, by way of example only, be generally dome shaped. The three-dimensional embroidered structure may be achieved by stitching thread pairs and enclosing thread pairs, which form the embroidered structure, in paths longer than the shortest distance between the endpoints of each thread pair. This extra thread length may be laid down and stored on the dissolvable substrate upon which the embroidering may be done by stitching the thread pairs in a zigzagging or otherwise meandering path. Once the dissolvable substrate is removed, the extra thread pair length relaxes from the zigzag path into a straight run of thread. This relaxation causes the two-dimensional zigzagging thread pair to become a three-dimensional structure-dependent shape, e.g. straight, curved, arcuate, or any combination thereof, as the length stored in the zigzagging path between its two fixed endpoints is conserved in the length between the same two fixed endpoints.

By way of example only, the summation of all the structure-dependent shaped thread pairs may form a dome-shaped embroidered structure. This dome effect may be enhanced by adding straight embroidered threads around the outside borders of the zigzagged area or, if the zigzagged area is surrounded by a uniform straight mesh, then around those borders. This straight embroidered thread border may be rigid and thus may prevent the zigzagged embroidered threads from expanding radially and thereby force them into a more pronounced dome shape.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The process of creating three-dimensional structures by embroidering with zigzagging thread pairs disclosed herein boasts a variety of inventive features and components that warrant patent protection, both individually and in combination.

Figure 1:
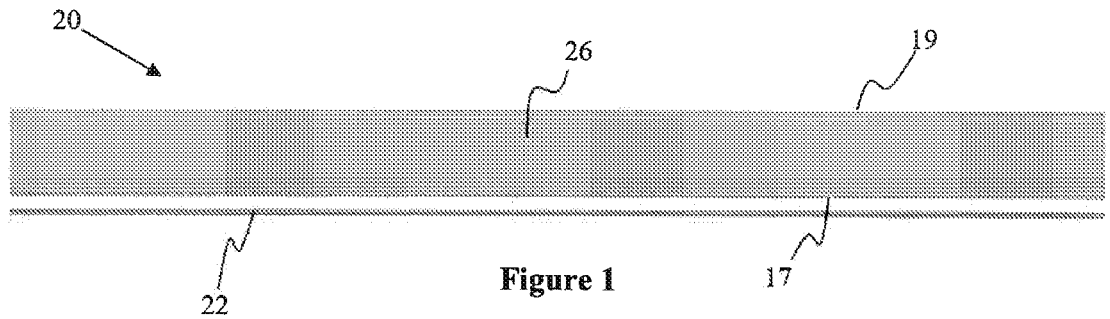
FIG. 1 illustrates a standard preparation of substrate and backing thread before stitching.

FIG. 1 illustrates a backing thread 22 placed and secured on the backing surface 17 of a dissolvable substrate 26. The threads used may be formed from any suitable material for creating an embroidered structure, including but not limited to polyester, polypropylene, polyethylene, carbon fiber, glass, glass fiber, polyaramide, metal, copolymers, polylactic acid, polyglycolic acid, biodegradable fibers, silk, cellulosic and polycaprolactone, including mixtures of one or more of these materials including fibers made therefrom. The dissolvable substrate 26 may be formed from acetate or any other material suitable for use as a dissolvable embroidery substrate. Dissolvable substrate materials are chosen such that the dissolution process or processes used to remove the dissolvable substrate 26 will have minimal effects on the physical properties of the materials of the embroidered structure which are designed to remain after dissolution.

Figure 2A:
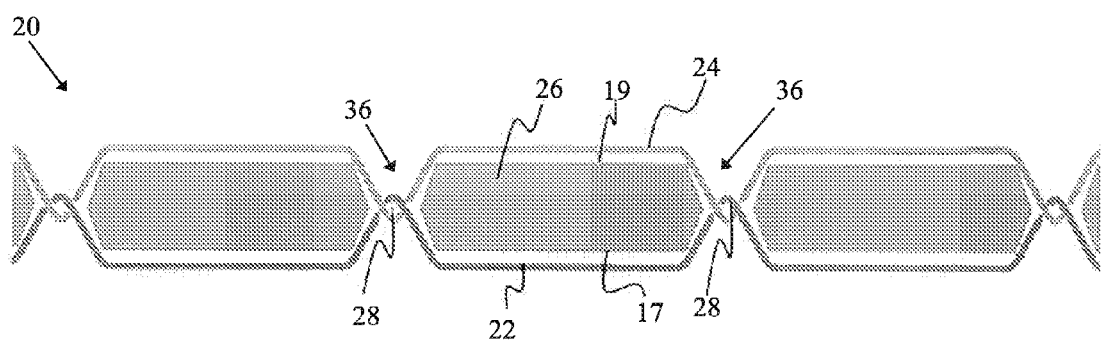
FIG. 2A depicts the standard preparation of FIG. 1 after lock stitches are formed between the backing thread from FIG. 1 and a corresponding stitching thread.

FIG. 2A illustrates the thread 20 as drawn in FIG. 1 after stitching to the backing thread 22. For each backing thread 22 on the backing surface 17 of the dissolvable substrate 26 there is a corresponding stitching thread 24 on the stitching surface 19. The stitching threads 24 from the stitching surface 19 are passed through openings 36 created in the substrate 26 by the passing of each individual stitching thread 24, to the backing surface 17. Each stitching thread 24 is then looped over its corresponding backing thread 22, forming a lock stitch 28. Once each stitching thread 24 has formed a lock stitch 28 with its corresponding backing thread 22, the stitching threads 24 are passed from the backing surface 17 to stitching surface 19 through the openings 36 in the substrate 26 created by the passing of the stitching threads 24 to the backing surface 17. The lock stitches 28 prevent the stitching threads 24 from completely pulling back out of the openings 36 created in the substrate 36. The stitching threads 24 are then moved to a new stitching site and the process repeats until each backing thread 22 is joined by lock stitches 28 to its corresponding stitching thread 24, creating a thread pair 20 of some desired length.

Figure 2B:
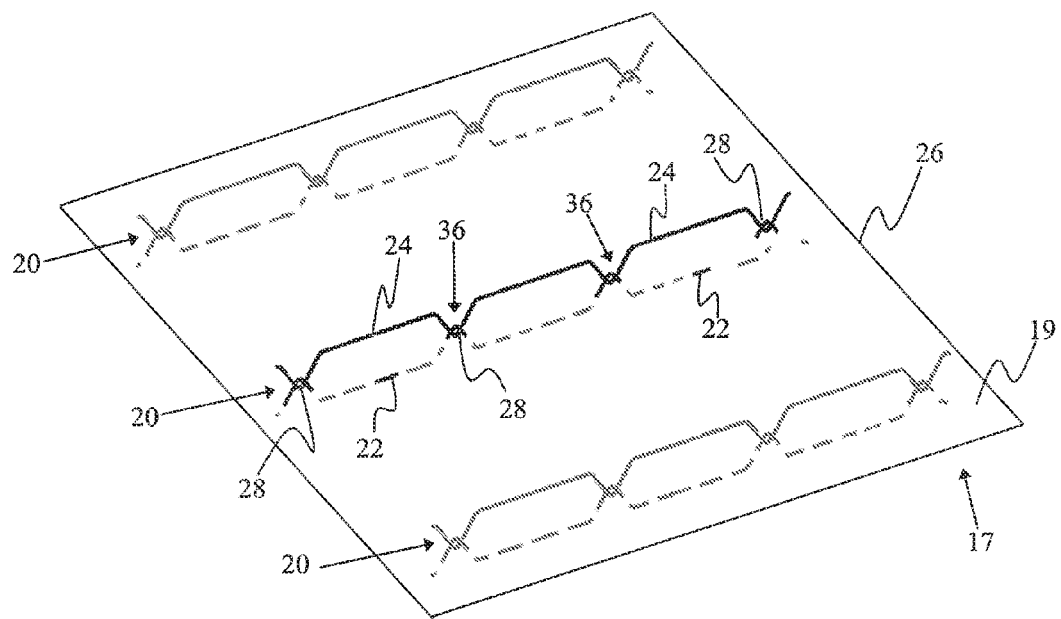
FIG. 2B is a perspective view of a dissolvable substrate upon which multiple thread pairs such as those depicted in FIG. 2A have been stitched.

FIG. 2B illustrates the result of the stitching process. The stitching threads 24 are now stitched to backing threads 22 in thread pairs 20 held together by lock stitches 28 on the dissolvable substrate 26. The stitched thread pairs 20 may then be enclosed by enclosing thread pairs.

Figure 3:
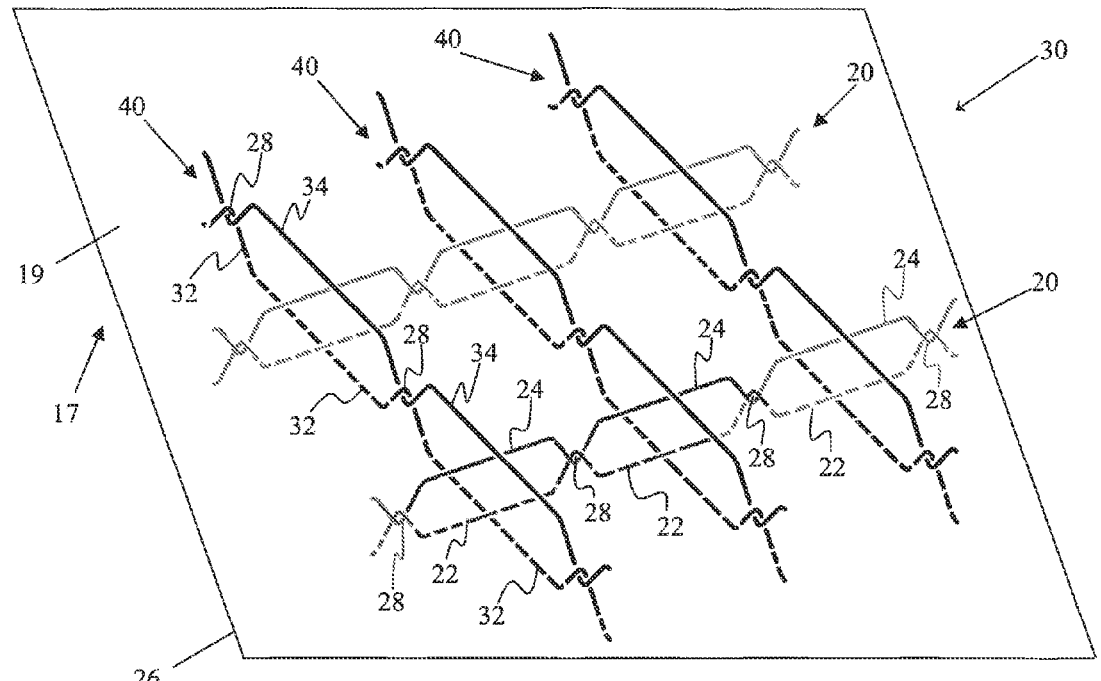
FIG. 3 is a representation of how straight biaxial stitched pairs of thread form embroidered structures.

FIG. 3 depicts the embroidered structure 30 created by enclosing the thread pairs 20 from FIG. 2B with enclosing thread pairs 40. The enclosing thread pairs 40 contain enclosing backing threads 32 and enclosing stitching threads 34. The enclosing backing threads 32 are placed and secured on the backing surface 17 of the substrate 26 over the backing threads 22 of the thread pairs 20. The enclosing stitching threads 34 are stitched from over the thread pairs 24 on the stitching surface 19 of the substrate 26 by the same stitching process discussed above. The result is an embroidered structure 30 where thread pairs 20 are enclosed within enclosing thread pairs 40. The embroidered structure 30 shown is enclosed by only one plurality of enclosing thread pairs 40, however, the same stitching process or a different stitching process may be repeated or performed one or more times using the same or different thread materials to enclose thread pairs 20 and any previously stitched enclosing thread pairs 40 by multiple pluralities of enclosing thread pairs 40 such that each plurality of enclosing thread pairs 40 encloses all thread pairs 20 and enclosing thread pairs 40 which were previously embroidered.

Figure 4:
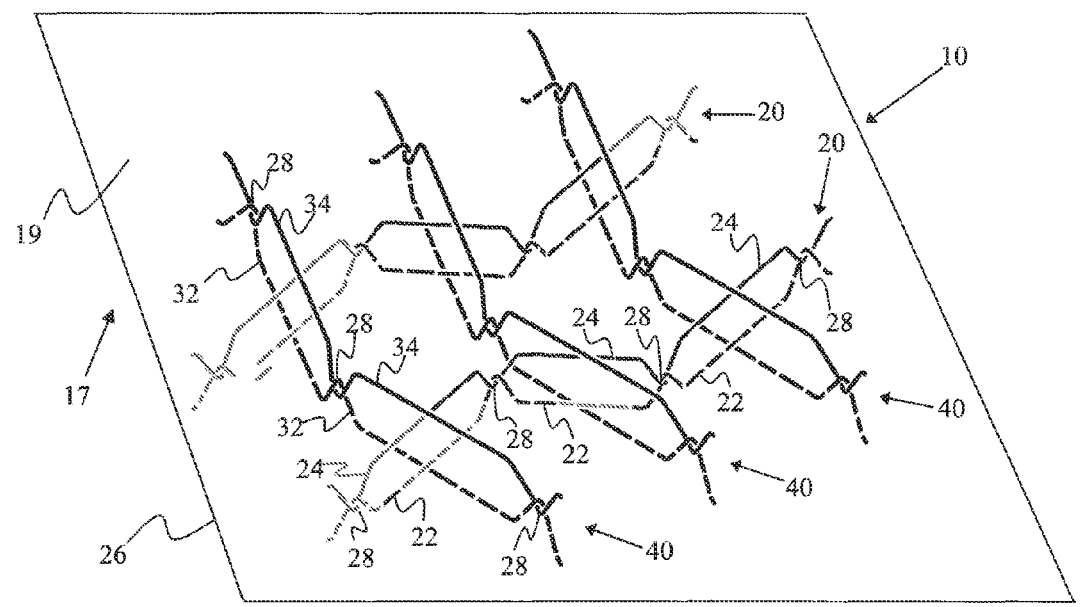
FIG. 4 is a representation of how zigzagging biaxial stitched pairs of thread form embroidered structures.

FIG. 4 shows the embroidered structure 10, which is the zigzagging corollary to the embroidered structure 30 from FIG. 3. Using the same stitching processes described above, the embroidered structure 10 is formed by laying down the backing threads 22 in a zigzag pattern and then following this zigzagging with the stitching thread 24 during the stitching process. The enclosing thread pairs 40 (only one plurality shown) are also stitched as described above, save for the enclosing backing threads 32 being laid down in a zigzag pattern and the enclosing stitching threads 34 following this zigzagging during the stitching process.

Figure 5A:
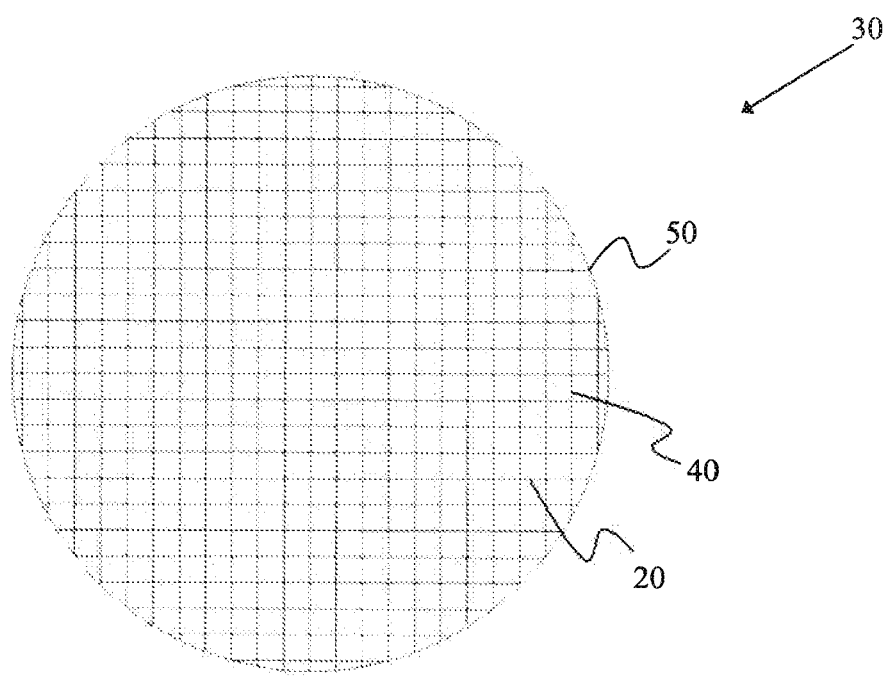
FIG. 5A is a plan view of a generally circular embroidered structure formed using straight biaxial stitched thread pairs.

FIG. 5A depicts a generally circular area of biaxial embroidered construction formed with straight thread pairs 20 and enclosed by straight enclosing thread pairs 40 to form the embroidered structure 30. The process of formation of the embroidered structure 30 is described above. The generally circular area is bounded by a rigid embroidered border 50 within which the thread pairs 20 and enclosing thread pairs 40 are orthogonal to each other on paths defined by the shortest distance between the endpoints of each thread pair 20 or enclosing thread pair 40.

Figure 5B:
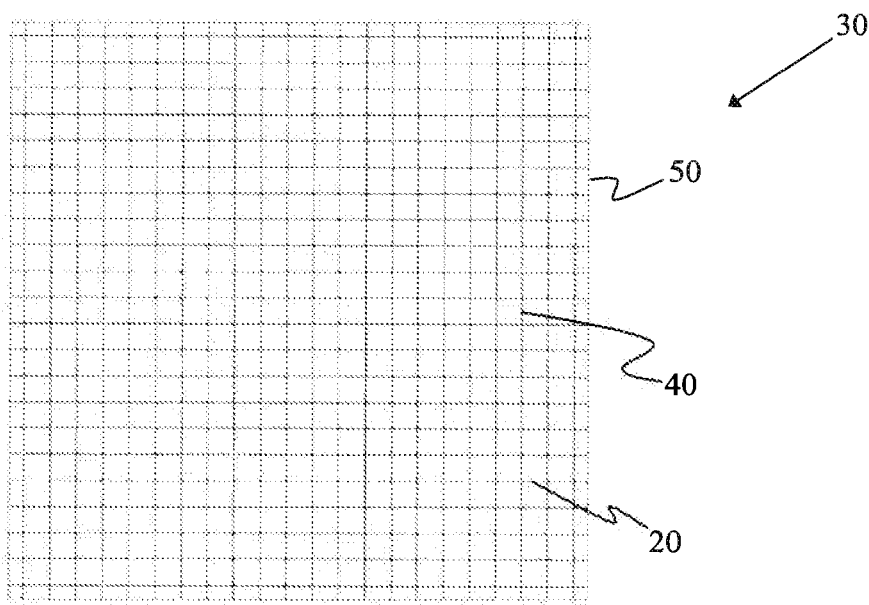
FIG. 5B is a plan view of a generally polygonal embroidered structure formed using straight biaxial stitched thread pairs.

FIG. 5B depicts a generally polygonal area of biaxial embroidered construction formed with straight thread pairs 20 and enclosed by straight enclosing thread pairs 40 to form the embroidered structure 30. The process of formation of the embroidered structure 30 is described above. The generally polygonal area is bounded by a rigid embroidered border 50 within which the thread pairs 20 and enclosing thread pairs 40 are orthogonal to each other on paths defined by the shorted distance between the endpoints of each thread pair 20 or enclosing thread pair 40.

Figure 5C:
FIG. 5C is a cross-sectional representation of the embroidered structures depicted in FIG. 5A and FIG. 5B after removal of the dissolvable substrate.

FIG. 5C is a representative cross-section of embroidered structure 30 of FIG. 5A and FIG. 5B after the substrate upon which the embroidered structure 30 was formed has been removed. Since the length of the thread pairs and enclosing thread pairs of the embroidered structures 30 depicted in FIGS. 5A and 5B are equal to the closest linear distance between the endpoints of the thread pairs and enclosing thread pairs, as in the embroidered structure 30 of FIG. 3, there is no extra length of embroidered thread to form a three-dimensional embroidered structure when the dissolvable substrate is removed. Therefore, the substrate upon which the embroidered structure 30 was formed with will retain the generally flat, two-dimensional shape it took during formation on the dissolvable substrate.

Figure 6A:
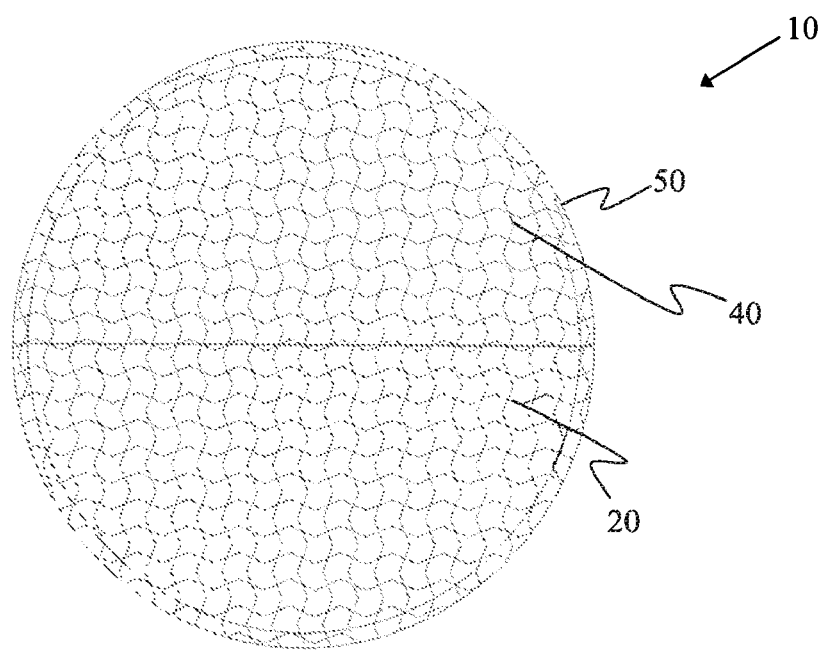
FIG. 6A is a plan view of a generally circular embroidered structure with a rigid border formed using zigzagging biaxial stitched thread pairs.

FIG. 6A depicts a generally circular area of biaxial embroidered construction formed with zigzagging thread pairs 20 and enclosed by zigzagging enclosing thread pairs 40 to form the embroidered structure 10. The process of formation of the embroidered structure 10 is described above. The generally circular area is bounded by a rigid embroidered border 50 within which the thread pairs 20 and enclosing thread pairs 40 are generally orthogonal to each other on paths which zigzag between the endpoints of each thread pair 20 or enclosing thread pair 40.

Figure 6B:
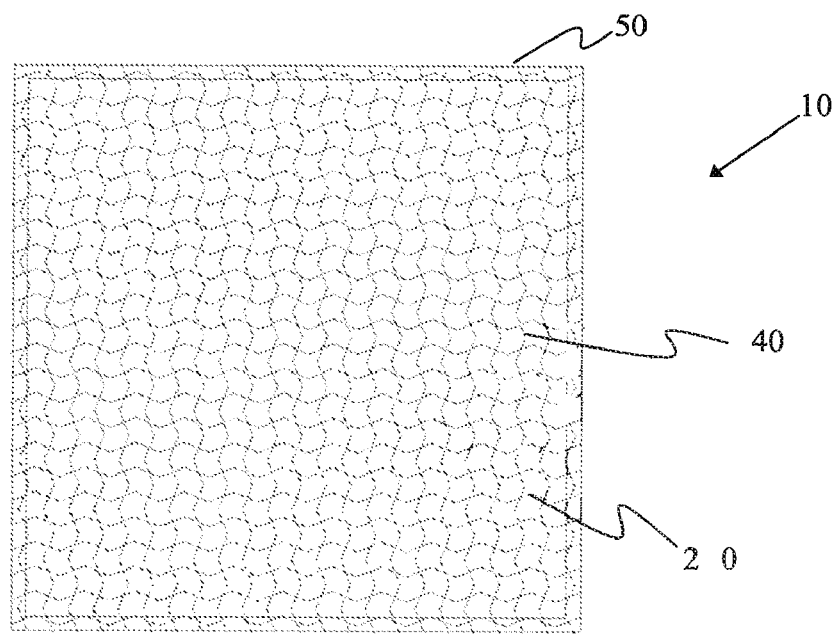
FIG. 6B. is a plan view of a generally polygonal embroidered structure with a rigid border formed using zigzagging biaxial stitched thread pairs.

FIG. 6B depicts a generally polygonal area of biaxial embroidered construction formed with zigzagging thread pairs 20 and enclosed by zigzagging enclosing thread pairs 40 to form the embroidered structure 10. The process of formation of the embroidered structure 10 is described above. The generally polygonal area is bounded by a rigid embroidered border 50 within which the thread pairs 20 and enclosing thread pairs 40 are generally orthogonal to each other on paths which zigzag between the endpoints of each thread pair 20 or enclosing thread pair 40.

Figure 6C:
FIG. 6C is a cross-sectional representation of the embroidered structures depicted in FIG. 6A and FIG. 6B after removal of the dissolvable substrate.

FIG. 6C is a representative cross-section of embroidered structure 10 of FIG. 6A and FIG. 6B after the substrate upon which the embroidered structure 10 was formed has been removed. The length of the thread pairs and enclosing thread pairs of the embroidered structures 10 depicted in FIG. 6A and 68 are longer than the closest linear distance between the endpoints of the thread pairs and enclosing thread pairs, as in the embroidered structure 10 of FIG. 4. When the extra length of thread is no longer held in a zigzag path by the dissolvable substrate, the extra thread pair length relaxes from the zigzag path into a straight run of thread. This relaxation causes the two-dimensional zigzagging thread pair to become a three-dimensional shape as the length stored in the zigzagging path between its two fixed endpoints is conserved in the length of the arc between the same two fixed endpoints. The summation of all the thread pairs forms a three dimensional embroidered structure. By way of example only, the three dimensional structure may be a dome. This three dimensional structure may be enhanced by adding straight embroidered threads around the outside borders of the zigzagged area or if the zigzagged area is surrounded by a uniform straight mesh, then around those borders. This straight embroidered thread border is rigid and thus prevents the zigzagged embroidered threads from expanding radially and forces them into a more pronounced three dimensional shape.

Figure 7A:
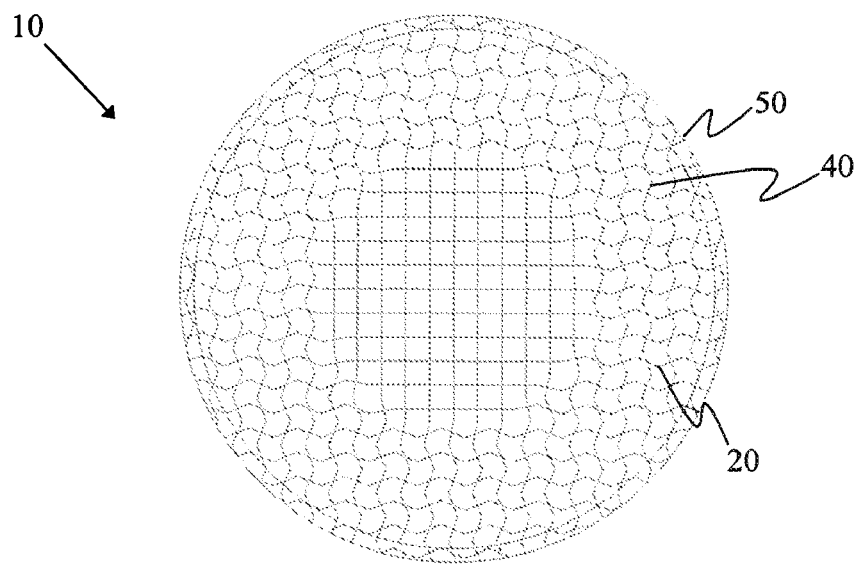
FIG. 7A is a plan view of a generally circular embroidered structure with a rigid border formed using both straight and zigzagging biaxial stitched thread pairs.

FIG. 7A depicts a generally circular area of biaxial embroidered construction formed by the processes described above. The central section of the generally circular area is composed of straight thread pairs 20 and straight enclosing thread pairs 40 as in FIG. 3 which is surrounded by an annular area composed of zigzagging thread pairs 20 and zigzagging enclosing thread pairs 40 as in FIG. 4. Rigid stitching of the perimeter completes the embroidered structure 1).

Figure 7B:
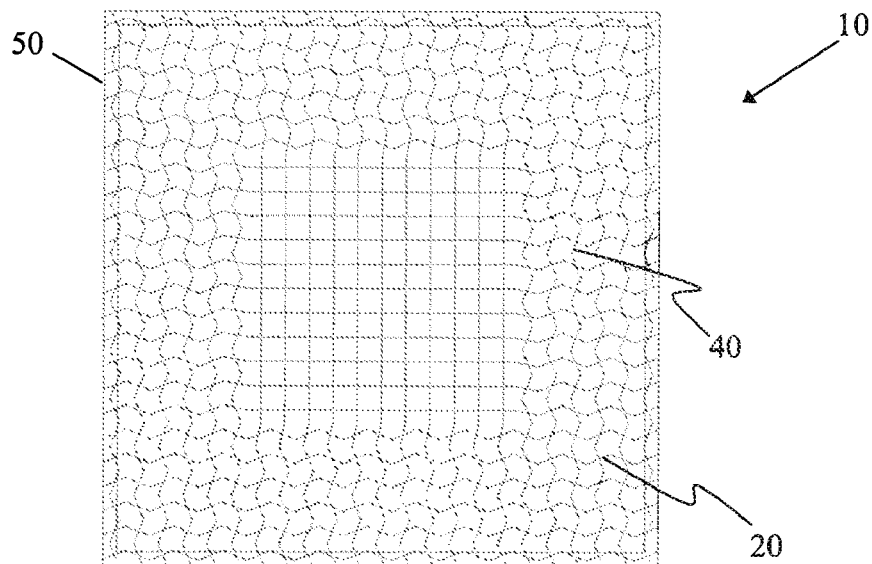
FIG. 7B is a plan view of a generally polygonal embroidered structure with a rigid border formed using both straight and zigzagging biaxial stitched thread pairs.

FIG. 7B depicts a generally polygonal area of biaxial embroidered construction formed by the process described above. The central section of the generally polygonal area is composed of straight thread pairs 20 and straight enclosing thread pairs 40 as in FIG. 3 which is surrounded an outer area composed of zigzagging thread pairs 20 and zigzagging enclosing thread pairs 40 as in FIG. 4 which covers the remaining polygonal area. Rigid stitching of the perimeter completes the embroidered structure 10.

Figure 7C:
FIG. 7C is a cross-sectional representation of the embroidered structures depicted in FIG. 7A and FIG. 7B after removal of the dissolvable substrate.

FIG. 7C is a representative cross-section of embroidered structure 10 of FIG. 7A and FIG. 7B after the substrate upon which the embroidered structure 10 was formed has been removed. Since the length of the thread pairs and enclosing thread pairs in the central region of the embroidered structure 1I are equal to the closest linear distance between the points defining the straight sections of thread pairs and enclosing thread pairs, there is no extra length of embroidered thread to relax into a three-dimensional shape when the dissolvable substrate is removed. Therefore, the central area of the embroidered structure 10 will retain the generally flat, two-dimensional shape it was given during formation on the dissolvable substrate. However, since the length of the thread pairs and enclosing thread pairs in the annular or outer region of the embroidered structure 10 depicted in FIG. 7A and 7B are longer than the closest linear distance between the endpoints of the sections of the thread pairs and enclosing thread pairs which zigzag, the extra length of zigzagging embroidered threads will relax from the zigzag path into a straight run of thread after the substrate upon which the embroidered structure 10 was formed was removed. This relaxation causes the two-dimensional zigzagging thread pairs to become three-dimensional sections of thread pair for the length between the two points where the thread pair zigzagged. The result is an embroidered structure which may, by way of example only, be domed around its periphery and flat through its central region. This peripheral dome effect may be enhanced by adding straight embroidered threads around the outside borders of the zigzagged area or if the zigzagged area is surrounded by a uniform straight mesh, then around those borders. This straight embroidered thread border is rigid and thus prevents the zigzagged embroidered threads from expanding radially and forces them into a more pronounced dome shape.

Figure 8A:
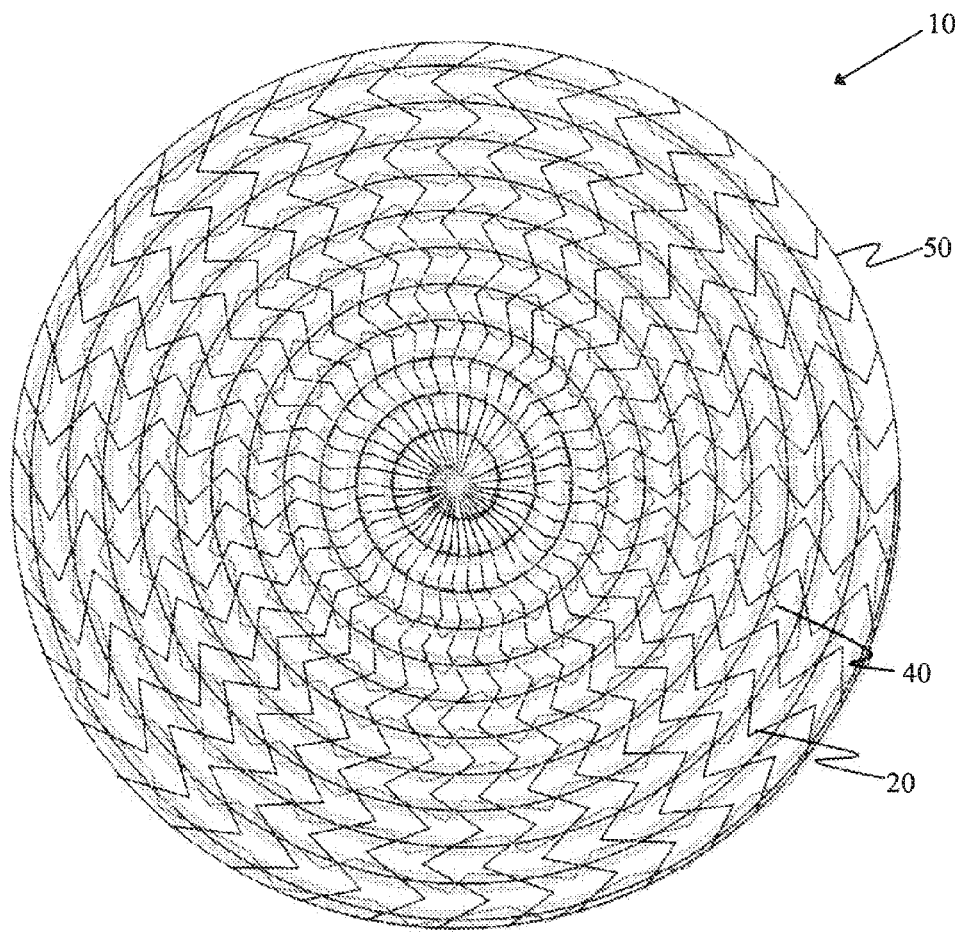
FIG. 8A is a plan view of a generally circular embroidered structure having both spiral and radial component layers of which each thread pair has a zigzagging path.

FIG. 8A is a plan view of a generally circular embroidered structure 10 formed with spiral and radial layers of thread pairs 20 and enclosing thread pairs 40, each of which is embroidered with a zigzagged path as in FIG. 4. The process of formation of the embroidered structure 10 is described above.

Figure 8B:
FIG. 8B is a cross-sectional representation of the curvature of the embroidered structure depicted in FIG. 8A after removal of the substrate.

FIG. 8B is a representative cross-section of FIG. 8A after the dissolvable substrate upon which the embroidered structure 10 was formed is removed. After the dissolvable substrate is removed, the embroidered structure 10 takes on a three-dimensional shape by the same relaxation mode as the embodiment depicted in FIG. 6C above.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A three-dimensional textile structure, comprising:
   a first portion comprising a plurality of thread pairs, each thread pair including a load-bearing thread interlocked with a backing thread, said textile structure being formed with each thread pair arranged in a two-dimensional zigzag manner along a dissolvable substrate between a first point and a second point such that upon removal of said substrate said thread pairs relax into a straight segment between said first and second points, forming a three-dimensional shape.

2. The three-dimensional structure of claim 1, wherein the structure comprises a bio-compatible structure suitable for attachment to at least one vertebra of a spine.

3. The three-dimensional structure of claim 1, wherein said load-bearing threads are formed of at least one of polyester, polypropylene, polyethylene, carbon fiber, glass, glass fiber, polyaramide, metal, copolymers, polylactic acid, polyglycolic acid, biodegradable fibers, silk, cellulosic, and polycaprolactone.

4. The three-dimensional structure of claim 1, wherein said load-bearing threads and said backing threads are interlocked by at least one of embroidery and weaving.

5. The three-dimensional structure of claim 1, further comprising:
   a second portion comprising a plurality of straight thread pairs bordering said first portion.

6. The three-dimensional structure of claim 1, wherein said three-dimensional shape comprises an arc.

7. A method of manufacturing a three-dimensional textile structure, comprising:
   (a) providing a dissolvable substrate having a stitching surface and a backing surface;
   (b) introducing a plurality of backing threads onto said backing surface, each backing thread introduced in a zigzag pattern between a first point and a second point on said substrate;
   (c) introducing a plurality of stitching threads onto said stitching surface, each stitching thread introduced in a zigzag pattern corresponding to one of said backing threads, said stitching threads and corresponding backing threads interlocked to form a plurality of thread pairs-arranged in a zigzag pattern on said substrate; and
   (d) dissolving said dissolvable substrate such that said thread pairs relax into a straight segment between said first and second points to form a three-dimensional structure.

8. The method of claim 7, wherein at least one of said stitching threads and said backing threads are formed of at least one of polyester, polypropylene, polyethylene, carbon fiber, glass, glass fiber, polyaramide, metal, copolymers, polylactic acid, polyglycolic acid, biodegradable fibers, silk, cellulosic, and polycaprolactone.

9. The method of claim 7, wherein step (c) further comprises interlocking said stitching threads and said backing threads by looping said stitching thread over said corresponding backing thread to form at least one lock stitch.

10. The method of claim 7, wherein the three-dimensional textile structure comprises a bio-compatible structure suitable for attachment to at least one vertebra of a spine.

\* \* \* \* \*